United States Patent [19]

Bruchman et al.

[11] Patent Number: 5,908,449
[45] Date of Patent: Jun. 1, 1999

[54] BLOOD CONTACT SURFACES USING EXTRACELLULAR MATRIX SYNTHESIZED IN VITRO

[75] Inventors: William Carl Bruchman; Paul Christopher Begovac, both of Flagstaff, Ariz.

[73] Assignee: W. L. Gore & Associates, Inc., Newark, Del.

[21] Appl. No.: 08/627,640

[22] Filed: Apr. 4, 1996

Related U.S. Application Data

[60] Division of application No. 08/424,839, Apr. 19, 1995, Pat. No. 5,716,394, which is a continuation-in-part of application No. 08/235,589, Apr. 29, 1994, abandoned.

[51] Int. Cl.$^6$ .................................................. A61F 2/06
[52] U.S. Cl. .................................. 623/2; 623/1; 623/11; 623/66
[58] Field of Search ............................... 623/1, 2, 11, 12, 623/66; 600/36; 435/240.23, 240.242, 177, 180; 424/424, 422

[56] References Cited

U.S. PATENT DOCUMENTS

| | | |
|---|---|---|
| 3,953,566 | 4/1976 | Gore . |
| 4,539,716 | 9/1985 | Bell . |
| 4,546,500 | 10/1985 | Bell . |
| 4,804,381 | 2/1989 | Turina et al. . |
| 4,804,382 | 2/1989 | Turina et al. . |
| 4,883,755 | 11/1989 | Carabasi et al. . |
| 4,960,423 | 10/1990 | Smith . |
| 5,037,378 | 8/1991 | Muller et al. . |

FOREIGN PATENT DOCUMENTS 531 547   3/1991   European Pat. Off. .

OTHER PUBLICATIONS

X. Yue et al., "Smooth Muscle Cell Seeding in Biodegradable Grafts in Rats: A New Method to Enhance the Process of Arterial Wall Regeneration," *Surgery* 103:206–12 (1988).

A. Schneider et al., "An Improved Method of Endothelial Seeding on Small Caliber Prosthetic Vascular Grafts Coated with Natural Extracellular Matrix," *Clin. Mat.* 13:51–55 (1993).

J. A. Madri et al., "The Collagenous Components of the Subendothelium," *Lab. Invest.* 43:303–15 (1980).

T. Matsuda et al., "A Hybrid Artificial Vascular Graft Based Upon an Organ Reconstruction Model: Significance and Design Criteria of an Artificial Basement Membrane," *ASAIO Transactions* 34:640–43 (1988).

R. G. Petty et al., "Endothelium–the Axis of Vascular Health and Disease," *J. Royal Coll. Phys. London* 23:92–102 (1989).

(List continued on next page.)

*Primary Examiner*—David Isabella
*Attorney, Agent, or Firm*—Eric J Sheets; David J Johns

[57] ABSTRACT

This invention is directed to improved blood contact devices such as vascular prostheses rendered substantially non-thrombogenic through addition of a preserved layer of extracellular subendothelial matrix. The preserved subendothelial matrix layer, which serves as the blood interface of the device, is analogous to the subendothelial matrix layer beneath the endothelium of native vascular surfaces. The device consists of a permanent synthetic base material, preferably porous expanded polytetrafluoroethylene, on which this biologic layer of subendothelial matrix is grown in situ. The biologic layer is produced using in vitro tissue culture methods whereby living cells synthesize and deposit extracellular matrix components, after which the cells are killed and/or removed and the subendothelial matrix layer preserved before implantation. A key aspect of this invention is that no living cells are present in the final configuration, so that the likelihood of recipient immunological response is minimized. This invention results in vascular prostheses that are particularly useful for arterial bypass requiring a diameter of 6 mm or less.

32 Claims, 5 Drawing Sheets

OTHER PUBLICATIONS

R. E. Scharf et al., "Thrombosis and Atherosclerosis: Regulatory Role of Interactions Among Blood Components and Endothelium," *Blut* 51:31–44 (1987).

S. M. Schwartz et al., "The Aortic Intima: II. Repair of the Aortic Lining After Mechanical Denudation," *Am. J. Pathol.* 81:15–42 (1975).

J. J. Zwaginga et al., "Thrombogenicity of Vascular Cells: Comparison between Endothelial Cells Isolated from Different Sources and Smooth Muscle Cells and Fibroblasts," *Arteriosclerosis* 10:437–48 (1990).

P. Colburn and V. Buonassisi, "Anti–clotting Activity of Endothelial Cell Cultures and Heparan Sulfate Proteoglycans," *Biochem. Biophys. Res. Comm.* 104:220–27 (1982).

I. Vlodavsky et al., "Platelet Interaction with the Extracellular Matrix Produced by Cultured Endothelial Cells: A Model to Study the Thrombogenicity of Isolated Subendothelial Basal Lamina," *Thromb. Res.* 28:179–91 (1982).

H. Miwa et al., "Development of a Hierarchically Structured Hybrid Vascular Graft Biomimicking Natural Arteries," *ASAIO Journal* 39:M273–77 (1993).

BLOOD CONTACT SURFACES USING EXTRACELLULAR MATRIX SYNTHESIZED IN VITRO

This is a divisional of application Ser. No. 08/424,839, filed on Apr. 19, 1995, now U.S. Pat. No. 5,716,394, which is a continuation-in-part application of Ser. No. 08/235,589, filed Apr. 29, 1994, abandoned.

BACKGROUND OF THE INVENTION

1. Field of the Invention

The present invention relates to improved blood contact surfaces for use in apparatus such as in artificial blood vessels and other implantable appliances, and methods for synthesizing the improved blood contact surfaces in vitro.

2. Description of Related Art

A common surgical practice in the treatment of occlusive atherosclerotic disease of peripheral arteries is to transplant a section of living vein, taken from the same patient, as a bypass around the occluded region of artery. Approximately one fourth of all patients requiring peripheral arterial bypass, however, have saphenous veins unsuitable for use because of varicosities, multibranching, or inadequate diameter. These patients then require some alternative material with which the bypass can be effected. In addition, the transplanted vein itself is often susceptible to the atherosclerotic disease process. This atherosclerotic process is similar to that of the artery but the vein is afflicted at an accelerated rate, frequently causing vein graft failure and necessitating an additional bypass. For these reasons, a need exists for a vascular substitute that would perform at least comparably to the autologous saphenous vein in the small diameter application.

In addition to autologous living tissues transferred from one location to another within the same individual, other biological materials have been used in this application. These include treated donor allogeneic or xenogeneic tissue components, such as processed human umbilical vein, cryopreserved allogenic vein, or processed xenogeneic artery. Although living vessel transplants from one patient to another are employed, the foreign vessel typically dies following transplant.

In addition to tissues of biological origin, synthetic materials are also commonly used to replace blood vessels. Synthetic vascular grafts have been used successfully since the 1950's to replace large vessels such as the aorta or iliac arteries. The principal synthetics used for grafting include polyethylene terephthalate and expanded polytetrafluoroethylene (ePTFE), although other materials utilized include polypropylene, polyurethane, and polydimethyl siloxane. Both porous and nonporous constructions of these polymers have been used.

Although both biologic and synthetic materials have been used with good success in some applications, such as bypasses from the femoral artery to the segment of the popliteal artery above the knee, both synthetic and biologic materials have been shown to thrombose much more frequently than the autologous saphenous vein when used for small diameter bypasses such as the coronary or below knee arteries. This performance difference limits the usefulness of such vascular replacements in these more demanding applications.

Natural blood contact surfaces, such as those found within blood vessels, have inherent mechanisms to prevent thrombosis during normal passage of blood along the surface. In the case of a mammalian artery, the immediate blood contact surface consists of a layer of endothelial cells that is non-thrombogenic. Immediately external to the endothelial cell layer is the remainder of the intima: a subendothelial matrix layer consisting of basement membrane and an underlying layer of glycoprotein-bearing extracellular matrix, and the internal elastic lamina. Surrounding the intima layer is the multilaminate media structure containing smooth muscle cells and elastin, and surrounding this, the most external layer, comprised of fibroblasts and connective tissue, the adventitia. As is explained in greater detail below, it is generally accepted that the subendothelial layer and media are thrombogenic in nature in order to maintain hemostasis when the vascular system is injured. See for example: J. A. Madri et al., "The Collagenous Components of the Subendothelium,"*Lab. Invest.* 43:303–15 (1980); and T. Matsuda et al., "A Hybrid Artificial Vascular Graft Based Upon an Organ Reconstruction Model:. Significance and Design Criteria of an Artificial Basement Membrane, "*ASAIO Transactions* 34:640–43 (1988).

Knowledge of the detailed mechanisms by which natural vessels maintain patency has been very limited. The predominate theory relating to the effective function of normal vasculature is based upon the necessity of a healthy, intact, vascular endothelium to serve as the blood interface. When the endothelial lining is removed, thrombosis of the vessel is a frequent occurrence. Supporting this theory, in part, are numerous experiments showing the endothelium to have a unique clot inhibiting effect on blood with which it is in direct contact. Endothelial cells have been further shown to synthesize or bind a number of substances with coagulation inhibiting or fibrinolytic function including heparan sulfate/antithrombin III, dermatan sulfate/heparin cofactor II, thrombomodulin/protein C/protein S, prostacyclin and tissue-type plasminogen activator. Thus, based on these experimental observations, and the blood contacting location of the endothelium in the vascular system, it has been widely accepted that the endothelium, is primarily, if not wholly, responsible for the antithrombotic behavior of blood vessels. See for example, R. G. Petty et al., "Endothelium-the Axis of Vascular Health and Disease," *J. Royal Coll. Phys. London* 23:92–102 (1989); and R. E. Scharf et al., "Thrombosis and Atherosclerosis: Regulatory Role of Interactions Among Blood Components and Endothelium," *Blut* 51:31–44 (1987).

In support of this concept, numerous experiments investigating the reactivity of blood to non-endothelialized vessels have been reported suggesting that the subendothelium and underlying structures are thrombogenic, particularly with respect to platelet adhesion and degranulation. These observations come from both in vivo and in vitro thrombosis assays.

In addition to the immediate subendothelial matrix layer, smooth muscle cells in the deeper media layer are generally considered to be thrombogenic as well. See for example, S. M. Schwartz et al., "The Aortic Intima: II. Repair of the Aortic Lining After Mechanical Denudation,"*Am. J. Pathol.* 81:5–42 (1975); J. J. Zwaginga et a., "Thrombogenicity of Vascular Cells: Comparison between Endothelial Cells Isolated from Different Sources and Smooth Muscle Cells and Fibroblasts," *Arteriosclerosis* 10:437–48 (1990). Evidence for this conclusion comes from studies where the addition of plasma to a culture of subendothelial cells including vascular smooth muscle cells has been shown to cause rapid, massive coagulation. In contrast, clotting was inhibited when the experiment was repeated with endothelial cell cultures, again emphasizing the nonthrombogenic nature of endothelial cells. See for example, P. Colburn and V. Buonassisi, "Anti-clotting Activity of Endothelial Cell Cultures and Heparan Sulfate Proteoglycans," *Biochem. Biophys. Res. Comm.* 104:220–27 (1982); and I. Vlodavsky et al., "Platelet Interaction with the Extracellular Matrix Produced by Cultured Endothelial Cells: A Model to Study the Thrombogenicity of Isolated Subendothelial Basal Lamina," *Thromb. Res.* 28:179–91 (1982).

The widely accepted interpretation of these observations of natural vessel function is that the endothelial cell lining of the vasculature is responsible for antithrombotic behavior and that the subendothelial layers as well as the smooth muscle cells found beneath the endothelium are thrombogenic so that hemostasis will result in the event of vessel disruption.

Not surprisingly, in an effort to, adapt the antithrombotic function of the endothelium to synthetic surfaces, specifically vascular grafts, most prior art references that utilize biological elements are directed toward providing a surface that will support an endothelial cell lining. For example, U.S. Pat. Nos. 4,539,716 and 4,546,500 issued to Bell disclose a method of constructing a living tubular prosthesis using a collagen gel to which cells are added. The cells serve as a contractile agent and are specified to be fibroblast cells, smooth muscle cells, or platelets. For an artery replacement, these patents specify the use of endothelium as the most internal layer, smooth muscle cells as the medial layer and a third layer cast of collagen and fibroblast cells. The endothelial cells employed are of unspecified origin.

In addition, U.S. Pat. Nos. 4,804,381 and 4,804,382 issued to Turina et al. describe a synthetic arterial vessel made with a microporous or semipermeable membrane, lined on the luminal side with a continuous layer of living endothelial cells to provide the blood interface, and coated on the outside with layers of smooth muscle cells to increase the viability of the live cells on the lumen and to impart elasticity.

A number of other U.S. Patents including, for example, U.S. Pat. Nos. 4,883,755 to Carabasi et al., 4,960,423 to Smith, and 5,037,378 to Muller et al., also describe means by which living endothelial cell coverage of vascular interfaces can be accomplished to produce antithrombogenicity. These approaches include endothelial cell sodding, the use of elastin-derived peptides, and simple physical means of applying endothelial cells to graft surfaces, respectively.

A structure similar to that of Bell, above, is taught by H. Miwa et al., "Development of a Hierarchically Structured Hybrid Vascular Graft Biomimicking Natural Arteries," *ASAIO Journal* 39:M273–77 (1993). En this case, smooth muscle cells are layered over a DACRON® graft in an applied artificial matrix of collagen type I and dermatan sulfate glycosaminoglycan. A layer of endothelial cells is then grown on the artificial matrix to serve as the blood contact surface.

Another approach to endothelialization of vascular grafts is disclosed by X. Yue et al., "Smooth Muscle Cell Seeding in Biodegradable Grafts in Eats: A New Method to Enhance the Process of Arterial Wall Regeneration," *Surgery* 103:206–12 (1988). These authors employ pre-clotted microporous, biodegradable, polyurethane vascular grafts seeded with nonautologous rat smooth muscle cells prior to implantation for use as the replacement of the abdominal aortas of living rats. This study attempts to generate a "neomedia" to strengthen a structure that would otherwise be mechanically insufficient following the resorption of the biodegradable graft material. The smooth muscle cell layer provides a surface upon which the hosts natural endothelial cells could spontaneously regenerate and cover the graft surface.

In another study,, for example, A. Schneider et al. used corneal endothelial cells to produce extracellular matrix on ePTFE vascular grafts. (A. Schneider el al., "An Improved Method of Endothelial Seeding on Small Caliber Prosthetic Vascular Grafts Coated with Natural Extracellular Matrix," *Clin. Mat.* 13:51–55 (1993)) After production of an extracellular matrix, these original cells were then removed using Triton X-100 and NH:OH and the tubes were seeded again with bovine aortic endothelium. This approach showed that endothelium could be successfully grown on the extracellular matrix lining the ePTFE grafts, but no implant studies were performed, however.

In all of the above described prior art references, the efforts are directed at achieving a living endothelial cell lining to provide nonthrombogenic function. Despite the above described efforts, substantial deficiencies still exist. In small diameter applications or grafts used in sensitive areas, for example, even limited thrombus generation is a very serious concern. It should also be noted that the vivo performance of the above endothelial cell-coated grafts has been highly variable, without a clear demonstration of enhanced patency over existing grafts.

Accordingly, it is a primary purpose of the present invention to provide an improved blood contact surface that is less thrombogenic than existing artificial surfaces and structures.

It is another purpose of the present invention to provide an artificial blood contact surface that can be readily manufactured and used.

It is a further purpose of the present invention to employ a previously unrecognized mechanism governing the interaction between blood and natural blood vessel structures and to produce an improved blood contact device and methods for making and using them.

These and other purposes of the present invention will become evident from review of the following specification.

SUMMARY OF THE INVENTION

The present invention is an improved blood contact surface suitable for use in a variety of appliances, including artificial blood vessels and other implantable blood contact devices.

This invention employs an extracellular matrix synthesized in situ by selected cells on synthetic surfaces. Surprisingly, this extracellular matrix emulates the antithrombotic properties of natural vessels and organs. The matrix is preferably produced in cell culture using cells derived from vascular tissue.

In a first step of the process, smooth muscle cells (SMCs) obtained from autologous, allogeneic, or xenogeneic sources are grown under mitogenic conditions, initially in culture dishes, then subsequently on the intended blood contact surface of a prosthesis until confluent coverage of the synthetic base material surface is largely achieved.

In a second step, the surface of the smooth muscle cell layer is seeded with endothelial cells derived from the surface of blood vessels. The two cell types are grown in co-culture on the surface of the prosthetic under growth conditions until an extracellular matrix is produced between the layers. This matrix is the analogue of the subendothelial matrix found in normal arterial vessels.

In a third step, the endothelial cells are removed so as to expose the subendothelial matrix overlying the SMCs. This is a key inventive feature as the prior art teaches directly away from this approach. As described in the background section above, the prior art teaches that endothelial cells are the appropriate blood contact surface. Thus, a key element of the present invention is a direct blood contact surface absent of living cells, especially endothelial cells. A further key element is the in vitro production of a subendothelial matrix analogue that results in an antithrombotic, non-immunogenic, vascular surface of desired size and shape. In the final steps, the subendothelial matrix may be preserved and sterilized using an appropriate fixative agent and a sterilizing agent, if necessary.

It will be recognized that artificial blood vessels are only one example of the high demand blood interface applications of this invention. Other possible applications include heart valves, artificial hearts, other artificial organs such as implantable artificial kidneys, and other direct blood contact appliances.

The present invention is a blood contact surface which comprises a synthetic base material, a layer of smooth muscle cells attached to the synthetic base material, and a layer attached to the smooth muscle cell layer comprising subendothelial mat substantially free of endothelial cells, wherein the subendothelial matrix layer serves as a direct blood contact surface.

DESCRIPTION OF THE DRAWINGS

The operation of the present invention should become apparent from the following description when considered in conjunction with the accompanying drawings.

DETAILED DESCRIPTION OF THE INVENTION

The present invention is directed to improved blood contact surfaces, such as those used in artificial blood vessels and other blood contact appliances.

Figure 1:
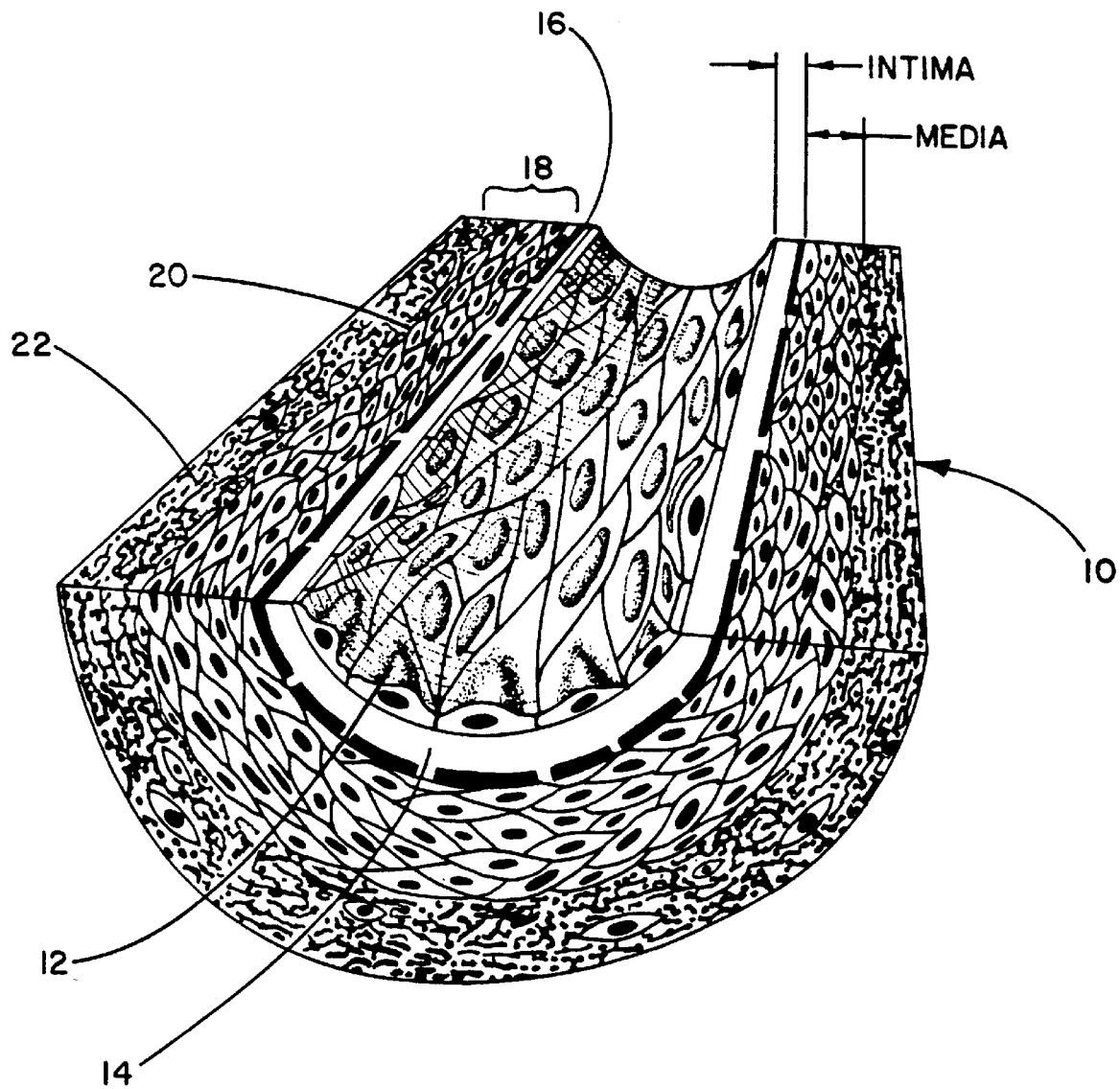
FIG. 1 is a perspective sectional view of a mammalian artery (10).
Figure 2:
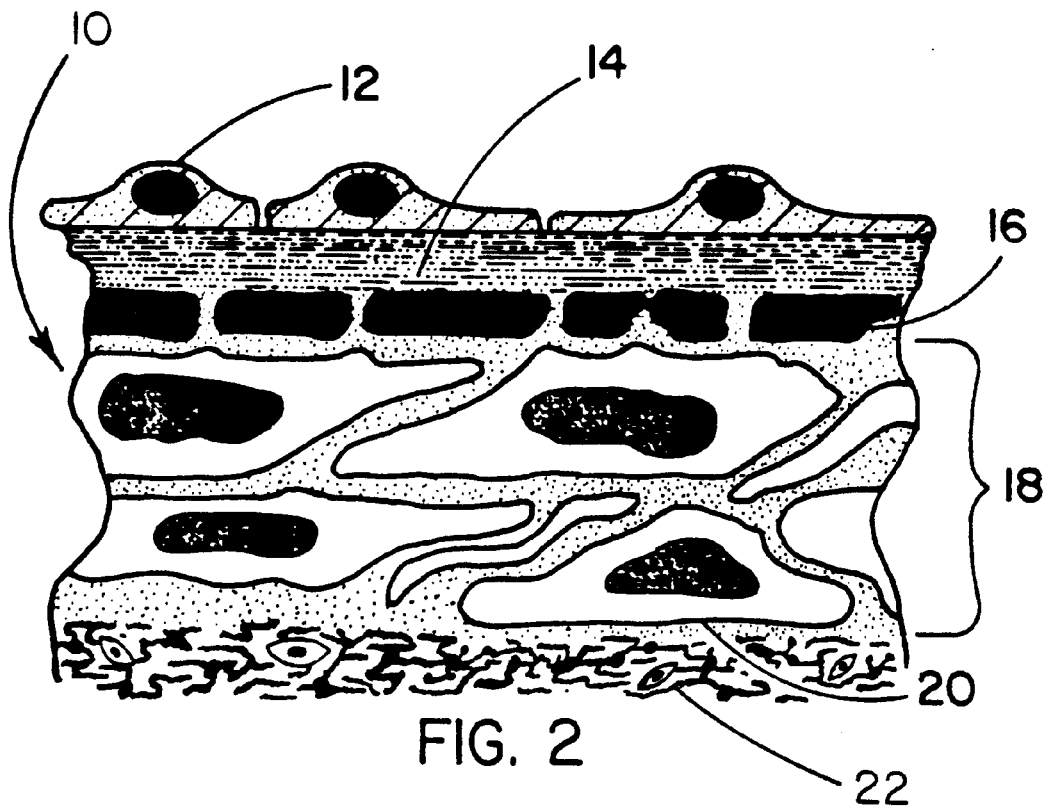
FIG. 2 is a sectional view through the longitudinal axis of a mammalian artery (10).

By way of introduction, FIGS. 1 and 2 illustrate the structure of a typical mammalian artery (10). The artery (20) structure consists of an intima layer having an innermost layer of endothelial cells (12), a subendothelial matrix layer (14) consisting of basement membrane and other extracellular matrix components, and an internal elastic lamina layer (16). External to the intima is a media layer (18) composed of smooth muscle cells (SMC) (20), and finally a fibrous connective tissue or adventitia layer (22).

As has been explained in the background section above, during normal blood flow the endothelial layer of cells (12) serves as the blood contact surface and, accordingly, must be nonthrombogenic. By contrast, when the blood vessel has been damaged, it is important that thrombosis occurs to prevent blood leakage from the vessel. In this respect, it has been generally accepted that the structures under the endothelial cell layer are thrombogenic in order to promote clotting wherever the endothelial layer has been compromised.

In contrast to the previous body of evidence in the prior art regarding blood vessel patency, it has been discovered that there is a mechanism independent of the living endothelium that contributes to the antithrombotic behavior of the vessel. Surprisingly, the location of this mechanism is not at the immediate blood contact surface of a native vessel but internal to the endothelial layer. This antithrombotic mechanism is dependent upon the subendothelial extracellular matrix previously reported in the prior art to be thrombogenic.

The present invention uses an analogue of the subendothelial matrix, synthesized with living vascular cells in vitro, to provide a substantially nonthrombogenic blood interface surface for synthetic materials. This subendothelial matrix is preferably produced by first culturing a substrate cell layer on a synthetic base, material for a period of time. It is preferred that the substrate cell layer be formed with smooth muscle cells (SMCs), and most preferably vascular smooth muscle cells (VSMCs). Once the substrate cell layer is created, it is seeded with endothelial cells (ECs), preferably of vascular origin, to re-establish a conventional vascular cell relationship. Following a culture period of sufficient time to allow both the SMCs and ECs to synthesize an in situ subendothelium, the ECs are specifically removed in such a manner as to leave the subendothelial matrix layer, substantially free of endothelial cells, overlying the SMCs on a synthetic base material. The goal of this treatment is to remove the endothelial cells while preserving the antithrombotic properties of the underlying extracellular matrix. It should be recognized that many of the methods commonly used to remove cells from culture surfaces will disrupt the layer of interest. Processes with the potential to alter the subendothelial matrix layer include exposure to enzymes such as trypsin or dispase, or exposure to detergents such as Triton X-100 or sodium dodecyl sulfate. The composite graft may then be stabilized by a fixation step, preferably using glutaraldehyde, to minimize immunogenicity and preserve the subendothelial matrix layer that will serve as a direct blood contact surface of the graft. The term "preserved subendothelial matrix layer," in the instant specification, refers to a subendothelial matrix layer, that has been treated with a fixative solution, such as glutaraldehyde, to chemically stabilize the matrix and thereby preserve the subendothelial matrix layer as a direct blood contact surface.

While the following examples are specific for vascular graft prosthetics, it should be recognized that artificial blood vessels are only one example of the high demand blood interface applications of this invention. Other applications to which this invention may be applied include heart valves, artificial hearts, and artificial organs such as implantable artificial kidneys among others.

As is explained in greater detail below, it has been shown that the use of the subendothelial matrix as a direct blood contact surface resolves many of the previous deficiencies of the prior art in creating substantially nonthrombogenic blood contact surfaces. First, the use of a natural subendothelial matrix layer is less prone to thrombus generation and other problems than presently available prosthetic grafts. This allows such grafts to be used in small diameter grafts and other applications that are particularly prone to thrombotic failure. Second, in artificial graft production, the provision of a natural subendothelial matrix layer as a substantially nonthrombogenic surface eliminates the need to provide a prosthesis having an endothelialized surface.

Preparation and Use of In Vitro Subendothelial Matrix

The source of subendothelial matrix for use in the present invention is based upon in vitro tissue culture methods. While the precise constituents producing antithrombogenicity are not yet fully understood, techniques have been developed that hold promise for producing the matrix on a large scale basis.

The natural generation of subendothelial matrix appears lo be the result of interaction between the endothelial cells (12) and the smooth muscle cells (20). In fact, it has been determined that a particularly effective blood contact surface can be generated in vitro by co-culturing a layer of smooth muscle cells with a layer of endothelial cells in tissue culture and allowing the co-cultured layers to form a subendothelial matrix layer between them. The steps of one process in this regard are illustrated in FIGS. 3 through 6.

The initial step in this process involves the preparation of a synthetic base material to support the smooth muscle cell layer. The preferred base material consists of a synthetic porous, expanded polytetrafluoroethylene (ePTFE) graft material, such as those commercially available from W. L. Gore & Associates, Inc., Flagstaff, Ariz., under the designation GORE-TEX® Vascular Graft. The 4 mm internal diameter vascular grafts used in the following description are commercially available product obtained from this source. The 2.5 mm internal diameter ePTFE, tubing used in following description were constructed from CD 123 fine powder P resin (ICI Americas) as taught in U.S. Pat. No. 3,953,566 to Gore, which is incorporated herein by reference. The tubes were expanded by stretching to produce a mean fibril length of 28 $\mu$m. A fibril length of less than about 60 $\mu$m is preferred for this application. The finished tubes had an internal diameter of about 2.5 mm and a wall thickness of about 0.33 mm.

The fibril length of the porous ePTFE tubes produced as above is defined herein as the average of ten measurements between nodes connected by fibrils in the direction of expansion. Ten measurements are made in the following manner. First, a photomicrograph is made of a representative portion of the sample surface, of adequate magnification to show at least five sequential fibrils within the length of the photograph. Two parallel lines are drawn across the length of the photomicrograph so as to divide the photograph into three equal areas, with the lines being drawn in the direction of expansion and parallel to the direction of orientation of the fibrils. Measuring from left to right, five measurements of fibril length are made along the top line in the photograph beginning with the first node to intersect the line near the left edge of the photograph and continuing with consecutive nodes intersecting the line. Five more measurements are made along the other line from right to left beginning with the first node to intersect the line on the right hand side of the photograph. The ten measurements obtained by this method are averaged to obtain the fibril length of the material.

Other suitable synthetic base materials may include but not be limited to the following: porous PTFE, polyethylene terephthalate, polypropylene, polyurethane and polydimethyl siloxane.

The synthetic base material suitable for the current invention was further prepared in the following manner. Commercially available 4 mm diameter GORE-TEX® Vascular Grafts (W. L. Gore & Associates, Inc., Flagstaff, Ariz.) and ePTFE tubing measuring 2.5 mm inside diameter were cut to 7 cm lengths and syringe fittings were tied to both the proximal and distal ends of the grafts. Each graft was then mounted in a stainless steel wire holder and a plug inserted into the connector at the distal end of the graft. After steam sterilization, the grafts were prepared for cell-seeding by wetting the normally hydrophobic ePTFE with 100% ethanol. The ethanol in the graft interstices was displaced with about 80–100 ml of Hanks' Balanced Salt Solution (HBSS) (Gibco BRL, Grand Island, N.Y.) using a syringe attached to the proximal connector. Wetted grafts were stored in HBSS until used for cell-seeding with smooth muscle cells.

Figure 3:
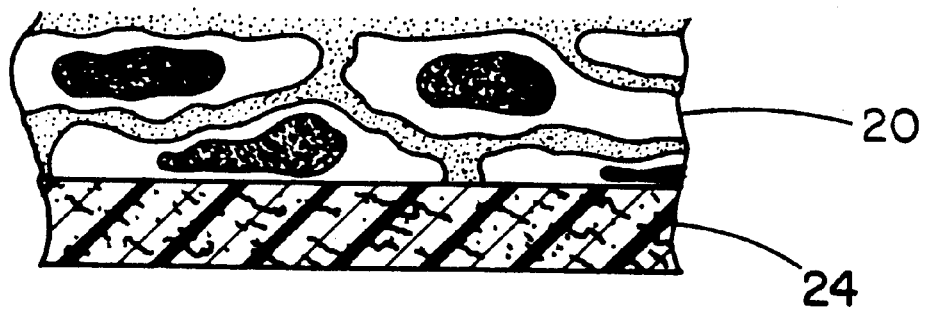
FIG. 3 is a cross-sectional view of a layer of smooth muscle cells (20) applied to a synthetic base material (24).

Once the base material tube has been prepared, SMCs (20) are applied to the luminal surface of the synthetic base material (24) producing a structure resembling that shown in FIG. 3. The preferred method is the use of positive pressure to force the SMCGM through the graft wall depositing SMCs onto the base material luminal surface. Other suitable means for applying the SMCs to the base material may include, but not be limited to: filling the base material tube lumen with a SMC suspension followed by a series of graft rotations to allow the SMCs to settle onto the surface uniformly; using negative pressure to draw the SMCs onto the substrate; and using chemotactic agents.

In several experiments, for example, the VSMCs were procured and applied to the synthetic base material in the following manner. Vascular SMCs were isolated by placing 3–4 cm segments of carotid or femoral arteries obtained from greyhound dogs into a tube containing cold, sterile Medium 199 and 50 $\mu$g/ml gentamicin (Gibco BRL). In a laminar flow hood, the artery segment was slit longitudinally and the endothelial cells were removed by first rubbing the luminal surface with a sterile paper towel followed by scraping with a #10 scalpel blade. Thin strips of arterial media were peeled up with forceps and pooled into a puddle of HBSS in a sterile Petri dish. The strips were then placed into 25 cm$^2$ tissue culture flasks containing 1.5 ml Smooth Muscle Cell Growth Medium (SMCGM; 43% Dulbecco's Modified Eagle Medium (DMEM); 43% Medium 199; 13% fetal bovine serum; 2 mM glutamine; 15 units/ml heparin; 23 $\mu$g/ml gentamicin; and 12.5 $\mu$g/ml endothelial cell growth supplement (Collaborative Biomedical Products, Bedford, Mass.)). Culture medium in the flasks was replaced when significant outgrowth of cells from the tissue pieces was observed. Cells were then fed 3–5 ml twice weekly, depending on the number of cells in the T-25 flask. Cells were generally passaged when about 60–90% confluent, and were usually split about 1:4. Smooth muscle cell type was confirmed by morphological criteria, positive staining for alpha smooth muscle cell actin, and lack of uptake of acetylated low density lipoprotein which would indicate endothelial cell (EC) contamination.

For graft-seeding purposes, subconfluent VSMC cultures (about passages 3–15) were rinsed briefly with calcium-magnesium-free-HBSS (CMF-HBSS) and washed in CMF-HBSS for about 3 to about 5 minutes. Cells were harvested using trypsin-ethylenediamine tetraacetic acid (trypsin-EDTA) to release cells from the flask, followed by trypsin neutralization with SMCGM. Cells were pelleted in a centrifuge at about 300×g for about 5 minutes and the pellet re-suspended in SMCGM for cell counting using a hemacytometer. After centrifugation, the cell pellet was re-suspended in SMCGM at a final concentration of about 2.5–6.0×10$^6$ cells per 6–8 ml and transferred into a syringe in preparation for graft seeding. Grafts having an internal diameter of 2.5 mm were seeded with about 2.5–3.5×10$^6$ cells/7 cm graft in about 6 ml SMCGM and 4.0 mm internal diameter grafts were seeded with about 4.0–6.0×10$^6$ cells/7 cm graft in about 8 ml SMCGM.

Smooth muscle cell seeding of a graft was performed by attaching the SMC-containing syringe to the proximal connector of the wetted graft and gently forcing the cell suspension into the graft and the media through the base material graft wall. The proximal fitting was then plugged and the smooth muscle cell seeded graft placed into a 16 mm culture tube filled with SMCGM with the graft wedged in the culture tube to prevent it from rolling in the tube. The culture tubes were capped securely and placed into an incubator at about 37° C. on a roller apparatus turning at about 10–50 rev/hr. The medium in the culture tubes was replaced at least twice weekly and grafts were cultured for a minimum of about ten days before further processing or the addition of endothelial cells.

Figure 4:
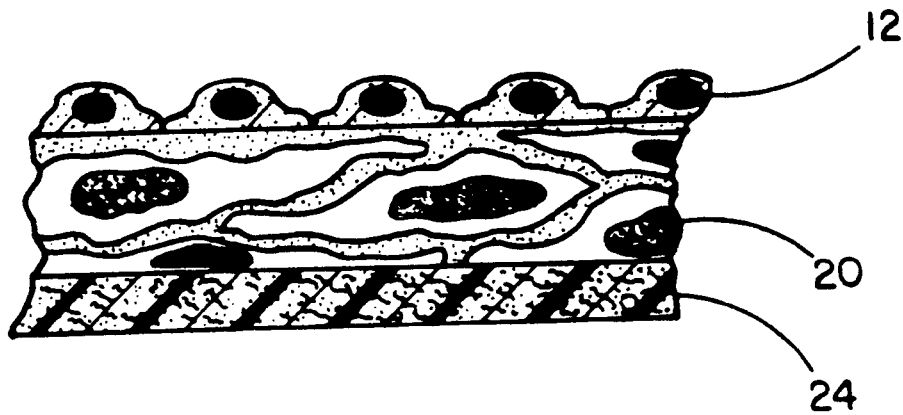
FIG. 4 is a cross-sectional view of a layer of endothelial cells (12) applied directly to a layer of smooth muscle cells (20) lying on a synthetic base material (24).

A layer of endothelial cells (12) attached to a substratum of smooth muscle cells 20 adhered to a synthetic base material (24) is shown in FIG. 4. This structure may be created in a variety of ways, with the preferred method being generating a single cell suspension of endothelial cells, filling the graft lumen with the suspension, and allowing the endothelial cells to attach, grow, and spread on the SMC surface to form a substantially confluent endothelial cell layer. Alternatively, small patches of endothelial cells may be directly harvested from a donor vessel and the patches seeded into the graft lumen whereby they attach and proliferate to cover the SMC layer.

One method to isolate endothelial cells (ECs) was by using enzymatic methods to release ECs from arterial or venous vessels obtained from dogs. The vessel lumina were cannulated in a laminar flow hood, rinsed with HBSS, and filled with an endothelial cell harvesting enzyme solution (for example, collagenase, dispase, trypsin, etc.) in CMF-HBSS for about 25 minutes at 37° C. Endothelial cells were flushed into a sterile centrifuge tube and the ECs pelleted at 30×g for 5 minutes. Cells were then plated onto T-25 tissue culture flasks and grown at 37° C. until nearly confluent, then passaged. Endothelial cell type was confirmed by morphological criteria, positive staining for Factor VIII, and uptake of acetylated low density lipoprotein.

For graft-seeding purposes, subconfluent endothelial cells (about passages 2–10) were rinsed briefly with CMF-HBSS and washed in CMF-HBSS for about 5 minutes. Cells were harvested by using trypsin-EDTA to release cells from the flasks followed by trypsin neutralization with complete Endothelial Cell Growth Media (ECGM; 80% Medium 199, 16% fetal bovine serum, 2 mM glutamine, 15 units/ml heparin, 25 μg/ml gentamicin, 12.5 μg/ml Endothelial Cell Growth Supplement (Collaborative Biomedical Products, Bedford, Mass.)). Cells were pelleted at about 30×g for about 5 minutes, and the pellet re-suspended in ECGM at a final concentration of 1.1–1.3×10$^6$ cells/ml. The cell suspension was transferred into a syringe.

A previously seeded SMC-graft (detailed above) was prepared for endothelial cell seeding by removing both end plugs and briefly rinsing the graft lumen with HBSS. The syringe containing the endothelial cell suspension was then attached to he proximal connector of the SMC-graft and the graft lumen filled with the cell suspension without forcing fluid through the graft wall. The syringe fittings were plugged and the grafts placed into 16 mm culture tubes filled with ECGM. Grafts were wedged into the tubes so they could not rotate independently of the culture tube.

Once the composite structure shown in FIG. 4 of endothelial cells (12) and smooth muscle cells (20) on a synthetic base material (24) is created, it is cultured. The following culture conditions have proven successful. Culture tubes were incubated at about 37° C. in a roller apparatus turning at about 10–50 revolutions/hr. The medium in the culture tubes was replaced at least twice weekly with ECGM for about 7 days to establish the ECs and then switched to SMCGM for the remainder of the culture period, a minimum of about 10 days total culture time.

Figure 5:
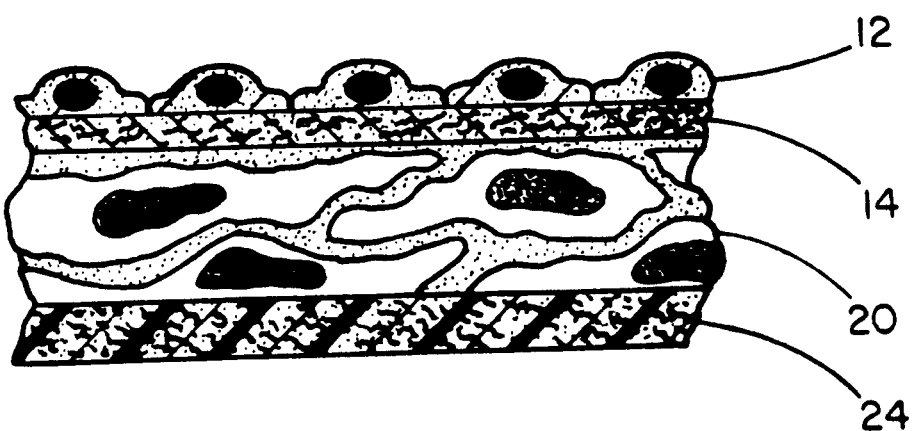
FIG. 5 is a cross-sectional view of the structure shown in FIG. 4 once a subendothelial matrix (14) has been generated between the endothelial cells (12) and the smooth muscle cells (20).
Figure 6:
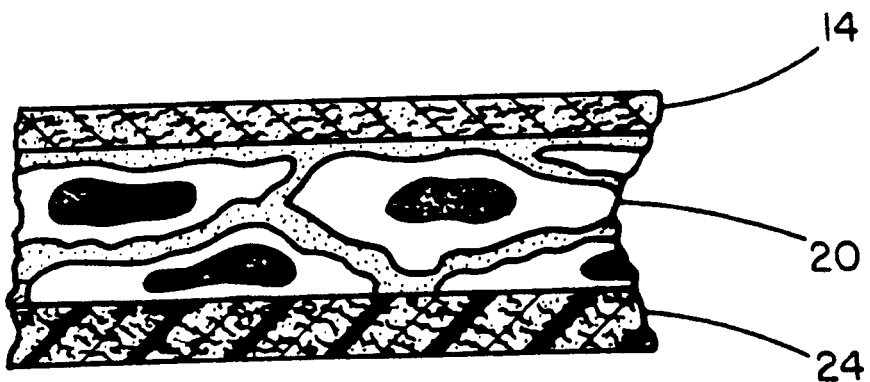
FIG. 6 is a cross-sectional view of one embodiment of the present invention wherein the endothelial cell layer (12) has been removed from the structure of FIG. 5.

Following culturing, a layer of subendothelial matrix (14) will form between the endothelial cells (12) and the smooth muscle cells (20) in the manner shown in FIG. 5. Generally the subendothelial matrix layer is less than about one μm in thickness.

Figure 7:
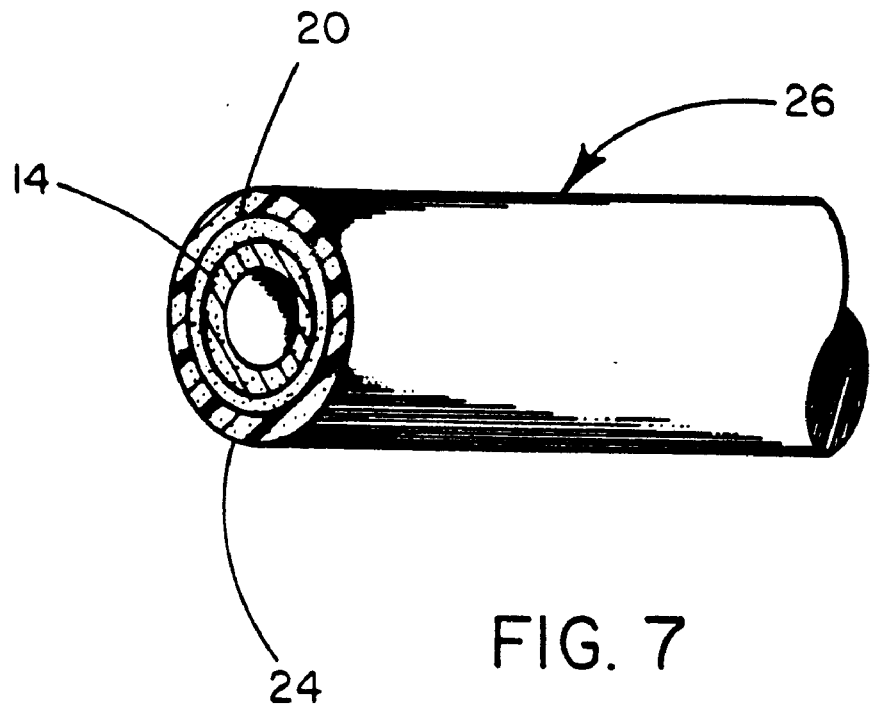
FIG. 7 is a view of a tubular embodiment (26) of the present invention illustrated in FIG. 6.

Once a suitable layer of subendothelial matrix (14) is created, the endothelial cell (12) layer is removed, such as through one of the following processes. Preferably, the endothelial cells are removed by rinsing the graft about three times with HBSS, treating the endothelialized surface with a stripping solution, such as, an ammonium hydroxide (NH$_4$OH) solution at a concentration of about 0.025 M, for about 4–4.5 minutes and rinsed again about three times in HBSS. Other suitable treatments may include NH$_4$OH at a concentration of about 0.01 to about 0.5 M for about 30 seconds to about 60 minutes. Other possibly effective methods of removing the endothelial cells include air drying, or treatment with other stripping solutions, for example, chloroform, methanol, sodium hydroxide, or sodium chloride, either alone or in combination. Other treatments known to those skilled in the an may also be suitable. Once the cell layer is removed, the structure resembles that shown in FIG. 6. FIG. 7 shows the structure of the tubular graft form 26 of one embodiment of the present invention.

Scanning electron microscopy inspection of representative samples treated in the above manner confirmed near total loss of the native endothelium and the maintenance of the subendothelial matrix layer. It is understood that for purposes of the present invention, removal of native endothelium from the subendothelial matrix layer in amounts greater than about 80% is considered to render the subendothelial matrix layer substantially free of donor endothelial cells.

The subendothelial matrix analogue exposed after removal of the endothelial cells contains numerous extracellular matrix components. Using immunocytochemical assays, it has been determined that the matrix contains chondroitin sulfate proteoglycans, collagen I, collagen III, collagen IV elastin, and fibronectin all of which are present both on the exposed blood contact surface as well as within portions of the graft wall. In addition, laminin is in abundant component of the subendothelial matrix blood contact surface and is present to a lesser degree within the graft wall.

Following EC removal, the grafts may be treated with a fixative to preserve the subendothelial matrix layer, to reduce immunogenicity, and to sterilize the graft. This fixation is accomplished by placing the graft into a fixing solution, such as, glutaraldehyde at a concentration of about 0.1–2.5%, for example, in a suitable buffer for about 1–72 hours depending upon the concentration of glutaraldehyde used. Suitable buffers may include N-2-hydroxyethylpiperazine-N'-2-ethane sulfonic acid (HEPES), acetate, 2-(N-morpholino) ethanesulfonic acid (MES), 3-[N-morpholino] propanesulfonic acid (MOPS), tris hydroxymethyl aminomethane, phosphate, and others. Other fixatives may also be suitable, such as, formaldehyde, dialdehyde starches, ethanol, and polyepoxy compounds, for example. Alternatively, the subendothelial matrix may be used without fixation.

In the preferred embodiment, the subendothelial matrix layer of the graft is fixed in greater than about 0.5% glutaraldehyde in 20 mM HEPES buffer for a minimum of about two hours. The fixed grafts are rinsed three times in sterile normal saline and washed for a minimum of about 24 hours in fresh sterile saline and then stored at about 4° C. Other suitable fixatives, such as formaldehyde, may be used in addition to glutaraldehyde to assure sterility, for example.

At this stage, a number of options exist for use of the subendothelial matrix 14. Given the nonthrombogenic nature of the subendothelial matrix (14), it is possible to implant the tubular graft structure substantially as shown in FIG. 7. Alternatively, the subendothelial matrix layer may be removed and directly applied to a damaged vessel in vivo. Further, in the case of autologous cells, the graft may be implanted with the cells in a viable state.

It is also possible to produce the subendothelial matrix layer through a variety of other methods. One suitable method, for example, involves using mixed culture seeding in which both ECs and SMCs are combined in ratios of 1:10 to 1:1 (EC:SMC) and both cell types are seeded onto the synthetic base material simultaneously. Once placed into culture, the ECs will form a confluent monolayer on the luminal surface thereby reestablishing the normal EC and SMC relationships. After extended co-culture, the subendothelial matrix is produced between the cell layers. The subendothelial matrix layer may then be exposed as outlined above and processed accordingly.

While VSMCs are the preferred use as the substrate cell layer in the production of the subendothelial matrix layer of the present invention, it is recognized that it may be possible to use other cell types to provide a similar function. Among the other potential cell types are smooth muscle cells from the digestive system or urinary tract, as well as fibroblasts, among others. It may also be possible to produce a suitable subendothelial matrix layer for use with the present invention through the use of other, non-living, base materials against which a subendothelial matrix layer may be formed by an attached endothelial cell layer.

Additionally, while vascular endothelial cells are the preferred embodiment, it may also be possible to use other endothelial cell types to produce the subendothelial matrix layer in conjunction with the VSMCs, SMCs, fibroblasts, or other similar cell types. These cell types may include, for example, microvascular endothelial cells, corneal endothelium, glomerular epithelium, and mesotheliar cells, among others.

Figure 8:
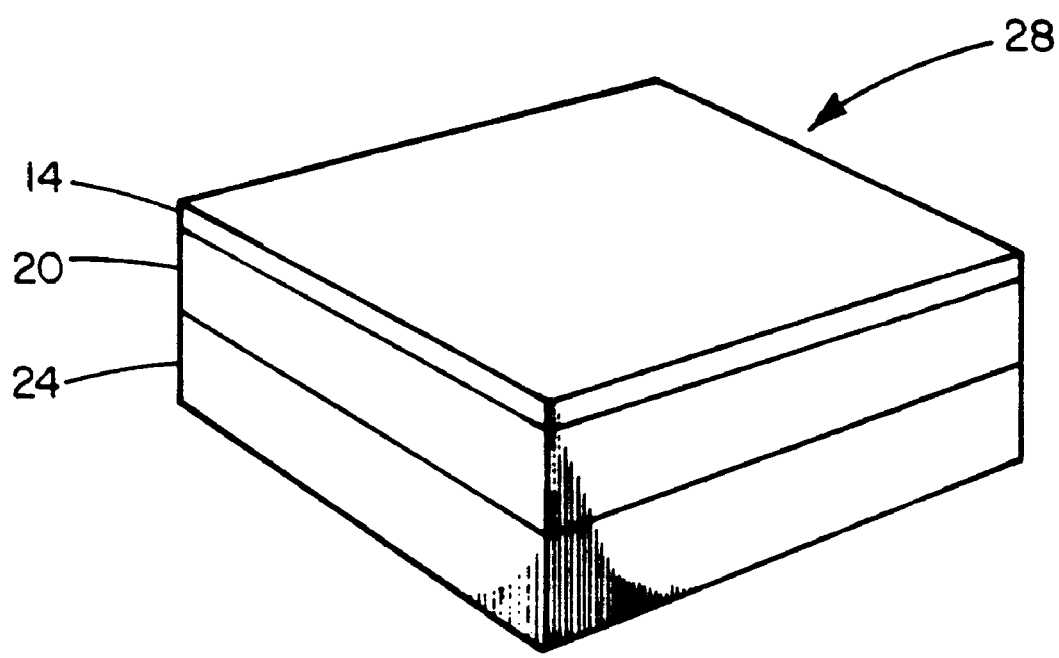
FIG. 8 is a view of one embodiment of the present invention wherein the structure shown in FIG. 6 is grown on a flat sheet of synthetic base material (24).
Figure 9:
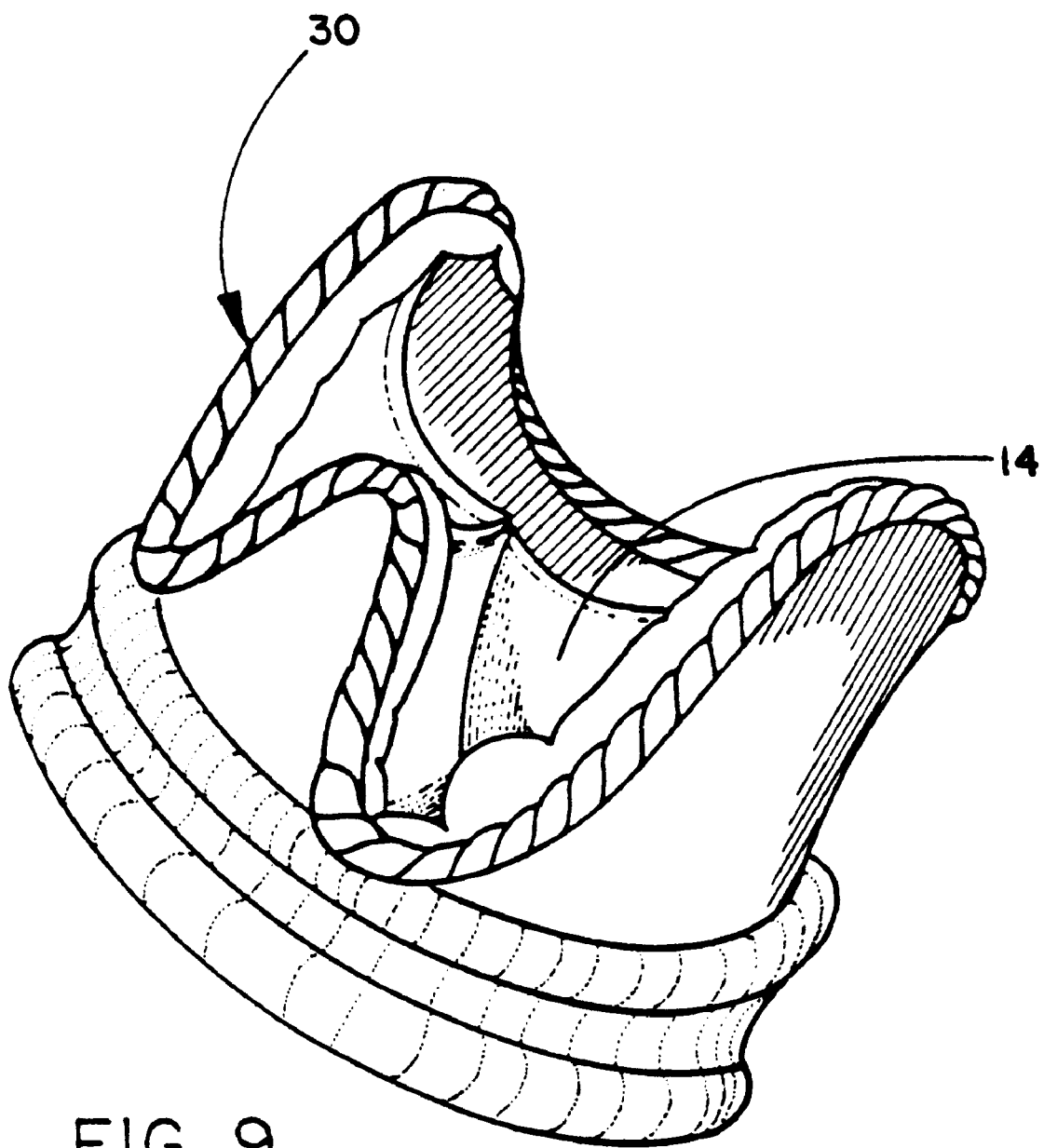
FIG. 9 is a view of a heart valve appliance (30) employing the subendothelial matrix (14) of the present invention.

It will be recognized that the present invention may be produced in different physical configurations depending upon the specific blood interface application. As shown in the structure of FIG. 8, it is possible to create the subendothelial matrix 14 on an SMC layer (20) on a synthetic base material (24) in a flat sheet form (28). Another application of the present invention shown in FIG. 9 includes the use of the subendothelial matrix layer (14) on the surfaces of a heart valve (30).

Without intending to limit the scope of the present invention, the following examples illustrate how the present invention can be made and used.

EXAMPLES

Example 1

The following is an example of grafts of the present invention (inventive grafts) compared to ePTFE grafts (control grafts) of the same diameter in implant studies. The inventive grafts were fabricated as described in the detailed description above. Briefly, endothelial cells (ECs) were seeded onto a vascular smooth muscle cell-covered (VSMC-covered) 2.5 mm ePTFE tube and cultured together for a minimum of 10 days. The inventive grafts were then treated for 30 seconds with 0.25 M $NH_4OH$ to remove the endothelial cells and rinsed by flushing with HBSS. After rinsing, the inventive grafts were fixed with 2.5% glutaldehyde in 0.2 M Sorenson's phosphate buffer (pH 7.0) for 2 hours. Following fixation, the grafts were rinsed in two changes of sterile normal saline, and stored at 4° C. in sterile normal saline until required for implantation.

The inventive and control grafts were implanted into greyhound dog brachial arteries as test pairs using a control graft consisting of a 2.5 mm diameter, 30 $\mu$M ePTFE tubing. One brachial artery received the inventive graft and the contralateral brachial artery received the 30 $\mu$m ePTFE control graft. The grafts, 2.5 cm in length, were implanted using standard end-to-end surgical technique. No anticoagulants or antiplatelet agents were administered at any time. Each dog was followed daily using a doppler ultrasound duplex scanner for the first two weeks postoperatively and weekly thereafter. Contrast angiography was also employed to determine patency status in the event of ambiguous ultrasound results. At one month, it was found that the inventive grafts were patent in three of six (3/6) cases and the ePTFE control grafts were patent in zero of six (0/6) cases. In conclusion, the inventive graft showed an improved patency performance compared to control ePTFE grafts of the same diameter.

Example 2

This is an example of an alternative method of fabricating the graft of the present invention described in Example 1 above. Individual cultures of vascular SMCs and ECs were harvested for graft fabrication by removing growth medium, rinsing the cells with CMF-HBSS, and washing the cells in CMF-HBSS for about 3–5 minutes. The CMF-HBSS was then removed and 2.5–3.0 ml of trypsin-EDTA (depending on flask size) was added to release cells from the flask. Complete SMCGM was added to the individual flasks to inactivate the trypsin, and the cells were triturated and pelleted by centrifugation at 300×g for 5 minutes. The supernatant was discarded, the cells were re-suspended in SMCGM, cell counts were carried out, and a second pelleting of cells was performed. The final individual SMC and EC cell pellets were re-suspended in SMCGM at a concentration of about $1 \times 10^6$ cells/ml. The cell types were mixed in EC:SMC ratios of 1:9, 1:4, and 1:2.

Synthetic base materials consisting of porous ePTFE tubes of 2.5 mm internal diameter and 30 $\mu$m fibril length were cut to 7 cm and mounted onto syringe connector fittings. A polypropylene plug was fatted onto the distal ends of the tube. The PTFE was wetted with 100% ethanol. The alcohol was then displaced with HBSS solution by pressurizing the tube, thereby forcing the HBSS through the porous tube wall. The wetted tubes were then stored in HBSS until seeding with the vascular cells.

The inventive graft was seeded with smooth muscle cells and endothelial cells, using positive pressure, by placing 2.5–3.5×10⁶ cells of the mixed SMC-EC suspensions into a total volume of about 6 ml SMCGM in a syringe. The 2.5 mm diameter size inventive graft was seeded with 2.5–3.5×10⁶ cells/7 cm graft. Cell numbers were quantified using a hemacytometer. The syringe containing the cell suspension was attached to the proximal syringe connector on the graft and the cell mixture was gently injected using positive pressure to force the media through the graft wall depositing the cells on the graft luminal surface. After placing cells into the graft, a second polypropylene plug was attached to the open connector to seal the cells in the graft luminal space.

The inventive seeded graft was placed into a 16 mm culture tube filled with SMCGM. The grafts were wedged in the culture tubes, capped securely, and placed in a roller apparatus turning at about 10 rev/hr. in a 37° C. incubator. Seeded grafts were cultured for 7 to 10 days with fresh medium feedings every 2–4 days. During this culture period, the endothelial cells were segregated from the SMCs forming a confluent EC monolayer on top of the SMCs. Scanning electron microscopy analysis and staining with acetylated low density lipoprotein were used to verify the presence of ECs on the graft luminal surface.

The inventive grafts were then rinsed three times with HBSS, and the lumen treated with 0.025 or 0.25 M NH₄OH for 4.5 and 3.5 minutes, respectively, to remove the ECs. The grafts were rinsed with HBSS, fixed with 0.25% glutaraldehyde for 24 hours at 23° C., followed by extensive washing in sterile normal saline. This resulted in the production of a subendothelial matrix layer similar to that produced in Example 1 described above.

Example 3

The following is an example of how the present invention may be practiced employing a substratum layer of fibroblast cells. A 30 μm ePTFE base tube was wetted with 100% ethanol and flushed with HBSS to displace the ethanol from the graft interstices. Dog foreskin fibroblasts were then harvested and applied to the graft surface using positive pressure to force the cells against the lumen of the graft wall. The graft was then placed into culture for a period of about 10–14 days. Following this, endothelial cells were seeded onto the fibroblast matrix surface by filling the graft lumen with a suspension of endothelial cells at a concentration of about 1.1–1.3×10⁶ cells/ml of ECGM. The graft was wedged into a culture tube and placed into a 37° C. incubator on a roller apparatus for at least 10 days to allow the endothelial cells to establish a monolayer and become firmly attached. Endothelial cell coverage was confirmed by observing uptake of acetylated Row density lipoprotein.

Following establishment of the endothelial cell-fibroblast co-culture to provide a subendothelial matrix layer, the endothelial cells were selectively removed by treatment with a stripping solution. After the endothelial cells were removed, the graft was fixed in glutaraldehyde to preserve, sterilize, and stabilize the subendothelial matrix. Following fixation, the graft is washed extensively with a sterile saline solution and stored in same until use.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A blood contact material wherein the material is formed through the following process:

culturing a first layer of smooth muscle cells on a synthetic base material;

culturing on the first layer of smooth muscle cells a layer of endothelial cells, the interaction of the smooth muscle cells and the endothelial cells forming a subendothelial matrix layer;

stripping the endothelial cell layer from the subendothelial matrix layer to produce a second layer comprised of a subendothelial matrix layer substantially free of endothelial cells; and employing the second layer as a direct blood contact surface.

2. The process of claim 1 which further comprises:

removing the second layer from the smooth muscle cells; and applying the second layer to a separate synthetic base material or recipient vascular tissue for use as a direct blood contact surface.

3. The process of claim 1 wherein the synthetic base material is selected from the group consisting of at least one of polytetrafluoroethylene, polyethylene terepthalate, fluorinated ethylene propylene, polyethylene, polypropylene, and siloxane.

4. The process of claim 1 which further comprises:

stripping the endothelial cell layer from the subendothelial matrix layer by treating the endothelial cell layer with a stripping solution.

5. The process of claim 4 wherein the stripping solution is selected from at least one of a group consisting of ammonium hydroxide, chloroform, methanol, and sodium chloride.

6. A blood contact material wherein the material is formed through the following process:

culturing a first layer of smooth muscle cells on a synthetic base material;

culturing on the first layer of smooth muscle cells a layer of endothelial cells, the interaction of the smooth muscle cells and the endothelial cells forming a subendothelial matrix layer;

stripping the endothelial cell layer from the subendothelial matrix layer to produce a second layer comprised of a subendothelial matrix layer substantially free of endothelial cells;

preserving the second layer; and employing the preserved second layer as a direct blood contact surface.

7. The process of claim 6 which further comprises:

removing the second layer from the smooth muscle cells; and applying the second layer to a separate synthetic base material or recipient vascular tissue for use as a direct blood contact surface.

8. The process of claim 6 wherein the synthetic base material is selected from the group consisting of at least one of polytetrafluoroethylene, polyethylene terepthalate, fluorinated ethylene propylene, polyethylene, polypropylene, and siloxane.

9. The process of claim 6 which further comprises:

stripping the endothelial cell layer from the subendothelial matrix layer by treating the endothelial cell layer with a stripping solution.

10. The process of claim 9 wherein the stripping solution is selected from at least one of a group consisting of ammonium hydroxide, chloroform, methanol, and sodium chloride.

11. A method for producing a direct blood contact material which comprises:

providing a layer of smooth muscle cells;

culturing on the layer of smooth muscle cells a layer of endothelial cells;

allowing a subendothelial matrix layer to form between the smooth muscle cells and the endothelial cells;

stripping away from the endothelial cell layer to expose the subendothelial matrix layer overlaying the smooth muscle cell layer; and employing the subendothelial matrix as the direct blood contact surface.

12. The method of claim 11 which further comprises:

forming the subendothelial matrix layer into a tubular appliance, the subendothelial matrix layer comprising an interior conduit for the appliance through which blood will flow.

13. The method of claim 11 which further comprises:

stripping away the endothelial cell layer by treating with a stripping solution.

14. The method of claim 13 wherein the stripping solution comprises an aqueous stripping solution of ammonium hydroxide at a concentration ranging from about 0.0 1 M to about 0.5 M.

15. The method of claim 11 that further comprises:

stripping away the endothelial cell layer by freeze-thaw treating the endothelial cell layer.

16. The method of claim 11 which further comprises:

stripping the endothelial cell layer by air dry treating the endothelial cell layer.

17. The method of claim 11 which further comprises:

removing the subendothelial matrix layer from the smooth muscle cell layer; and applying the subendothelial matrix layer to an appliance to serve as a direct blood contact surface thereon.

18. The method of claim 11 which further comprises:

preserving the exposed subendothelial matrix layer; and employing the preserved subendothelial matrix layer as a direct blood contact surface.

19. The method of claim 11 which further comprises:

treating the subendothelial matrix layer with a fixative solution to preserve the subendothelial matrix layer.

20. The method of claim 19 wherein the fixative solution is ethanol.

21. The method of claim 19 wherein the fixative solution is glutaraldehyde.

22. The method of claim 18 which prior to preserving the exposed subendothelial matrix layer further comprises:

removing the subendothelial matrix layer from the smooth muscle cell layer; and applying the subendothelial matrix layer to an appliance to serve as a direct blood contact surface thereon.

23. A method of making an implantable material having at least one blood contact surface comprising:

procuring vascular smooth muscle cells from a blood vessel;

placing the vascular smooth muscle cells onto a surface of a synthetic base material to form a coating of vascular smooth muscle cells thereon;

applying endothelial cells to the coating of vascular smooth muscle cells to form a layer of endothelial cells on the vascular smooth muscle cells;

culturing a subendothelial matrix layer between the endothelial cell layer and the vascular smooth muscle cell coating;

removing the endothelial cell layer to expose the subendothelial matrix layer overlying the smooth muscle cell layer, the subendothelial matrix layer being suitable for use as a direct blood contact surface.

24. The method of claim 23 which further comprises:

implanting the synthetic base material having the, coating of vascular smooth muscle cells and a subendothelial matrix layer applied thereto, so as to position the subendothelial matrix layer as a direct blood contact surface.

25. The method of claim 23 which further comprises:

removing the subendothelial matrix layer and applying the subendothelial matrix layer to the surface of another synthetic base material.

26. The method of claim 23 which further comprises:

providing synthetic base material in a form selected from a group consisting of a tubular form, the form of a sheet, a spherical form, and the form of a hollow container.

27. The method of claim 26 which further comprises:

providing the synthetic base material in the form of a porous polytetrafluoroethylene.

28. The method of claim 23 which further comprises:

culturing the vascular smooth muscle cells on the surface of a tube of porous polytetrafluoroethylene.

29. The method of claim 23 which further comprises:

culturing the vascular smooth muscle cells on the surface of a sheet of porous polytetrafluoroethylene.

30. The method of claim 23 which further comprises:

preserving the subendothelial matrix layer, the preserved subendothelial matrix layer being suitable for use as a direct blood contact surface.

31. The method of claim 30 which further comprises:

implanting the synthetic base material having the coating of vascular smooth muscle cells and a preserved subendothelial matrix layer applied thereto, so as to position the preserved subendothelial matrix layer as a direct blood contact surface.

32. The method of claim 30 which further comprises:

removing the subendothelial matrix layer and applying the subendothelial matrix layer to the surface of another synthetic base material, prior to preserving the subendothelial matrix layer.

* * * * *